United States Patent [19]

Kaplan

[11] Patent Number: 5,437,199
[45] Date of Patent: Aug. 1, 1995

[54] SAMPLING KIT FOR COMPRESSED AIR/GAS SOURCES

[76] Inventor: Larry Kaplan, 900 Bay Dr., Apt. No. 1001, Miami Beach, Fla. 33141

[21] Appl. No.: 197,207

[22] Filed: Feb. 16, 1994

[51] Int. Cl.⁶ .............................................. G01N 1/22
[52] U.S. Cl. .............................. 73/863.23; 73/863.57
[58] Field of Search ........... 73/863.23, 863.25, 863.31, 73/863.21, 863.61, 864.51, 864.62, 864.63, 863.57

[56] References Cited

U.S. PATENT DOCUMENTS

| | | | |
|---|---|---|---|
| 4,456,014 | 6/1984 | Buck et al. | 73/863.23 |
| 4,461,184 | 7/1984 | Gandhi et al. | 73/863.23 |
| 5,101,671 | 4/1992 | Elgas | 73/863.23 |

Primary Examiner—Hezron E. Williams
Assistant Examiner—Nashmiya Ashraf
Attorney, Agent, or Firm—Malin, Haley, DiMaggio & Crosby

[57] ABSTRACT

A portable kit for retrieving, storing, and transporting compressed breathing air samples obtained from compressed breathing air source tanks having pressures varying from 100 psi to 6,000 psi, the kit including a pair of quick-disconnect adapters that allow the inlet air flow conduit to be coupled to either a conventional scuba yoke to deliver breathing air or to a conventional fire fighting supply tank yoke, the system further including an air flow restrictor, a particulate air filter, and a vent for proper pressure regulation for use with a variety of supply pressures.

4 Claims, 4 Drawing Sheets

SAMPLING KIT FOR COMPRESSED AIR/GAS SOURCES

BACKGROUND OF THE INVENTION

1. Field of the Invention

This invention relates generally to an apparatus to retrieve, store, and ship gas samples obtained from high pressure compressed gas sources for laboratory analysis, and specifically, to an automatic compressed breathing air sample retrieval kit that is used to retrieve, store, and ship breathing air samples obtained from stored compressed breathing air tanks that are maintained under high pressure, up to 6,000 psi, and that are typically used to charge scuba tanks and fire fighters' breathing tanks.

2. Description of the Prior Art

The use of compressed breathing air in scuba tanks for scuba diving is well known. Most scuba tanks maintain compressed breathing air at 3,000 psi for use when diving. Since the compressed air is directly utilized and provides the only source of air for the diver, the air source must be free of deleterious contaminants and must contain the proper mixture of nitrogen and oxygen to insure safe breathing for the diver. Compressed air bottles and tanks are also used by fire fighting personnel for a source of breathing air in smoke-filled areas. Therefore, it is imperative that the air be clean of contaminants and in the proper ratios of nitrogen and oxygen to insure safe, healthy breathing for fire fighters.

Scuba tanks and fire fighting air tanks are periodically refilled from sources of air stored in large, high pressure tanks pressurized up to 6,000 psi. The source of air is typically provided by commercial establishments for filling scuba and fire fighter tanks. In order to insure that the air is of proper quality, it is necessary for them to periodically analyze air samples obtained from these large, high pressure storage tanks. This is done by collecting the samples from each supply tank of high pressure compressed air and sending them to outside laboratories for testing. For accurate measurement of the air quality, it is critical to know the volume of air sampled to measure contamination levels based on contaminants found in the filters. It is essential that the sample testing be done correctly and accurately and that the retrieved samples be stored in containers or environments suitable for shipment to laboratory test sites. Moreover, it is commercially important for businesses that samples retrieved be kept simple and efficient to increase reliability and to decrease cost since frequent sampling of the breathing air source is required.

U.S. Pat. No. 3,372,274, issued to R. R. Landolt Mar. 5, 1968, shows a gas sampler that collects inert radioactive fission gas. A flow meter is shown to determine the amount of gas received into the system for proper analysis. U.S. Pat. No. 4,576,054, issued to H. S. Lalin Mar. 18, 1986, shows a dual mode gas sampler and pneumatic flow control system that allows simultaneous testing of gas samples for multiple test articles, either under constant pressure or constant flow. The system shown includes an air pump and a regulating diaphragm. U.S. Pat. No. 4,073,619, issued to Lawson Feb. 14, 1978, shows a device for sampling gas for analysis. Many of such prior art devices are complex in their structure and operation, and are not really suitable for daily commercial operations requiring numerous periodical sampling.

The present invention provides a sampling kit for compressed breathing air that is non-complex, inexpensive, automatic, and useful for collecting air samples from high pressure (up to 6,000 psi) compressed air supply tanks. The kit includes sampling adapters that can be used to connect to different supply sources, such as scuba tank supply sources or fire fighter supply sources. The pressure of the source itself is not critical. The kit is also conveniently mounted in a housing that allows a sample to be easily taken and readily shipped to a point for analysis. The kit itself can even be shipped through the mail to the laboratory for testing.

Accordingly, the present invention is a relatively non-complex sample retrieval device that is contained in a small-volume package in kit form that can be used for obtaining air samples from compressed breathing air storage tanks that have a great pressure range.

SUMMARY OF THE INVENTION

The instant invention provides a compressed breathing air sample retrieving apparatus for obtaining representative quantified air samples from air storage tanks in the pressure range of 100 psi to 6,000 psi. The apparatus comprises a plastic-enclosed pouch for storing an air sample, an air flow conduit that is connectable between the source of air to be sampled and the pouch, a gas flow restrictor mounted within said air flow conduit between said air source and said pouch for reducing the air pressure in the air flow conduit, a particulate filter mounted downstream of said air restrictor for determining particulates in said air sample, an air vent connected to said air flow conduit downstream of said air restrictor for venting excess gas, and at least one mechanical sampling adapter removably connectable to the inlet end of said air flow conduit, said adapter being sized and matched to fit a fill station yoke at the supply tank to be tested. The air restrictor greatly reduces the air pressure within the air flow conduit and is mounted adjacent the inlet opening in the air flow conduit near the high pressure supply source to be sampled to. The enclosed pouch receives the air sample and includes a pressure relief valve so that the pressure within the pouch may be maintained within a certain limit. The gas vent in the system also insures that the pressure is not exceeded within the air flow line. The air restrictor is sized to allow the system to maintain a constant pressure while taking a sample for a fixed amount of time. Therefore, if one knows the fixed amount of time that the sample was taken and the pressure of the supply source, the correct volume of air measured and sampled can be determined for proper measurement and analysis of the air sample.

The apparatus may come in different sizes, depending on the anticipated source pressure of the supply tank. As an example, there can be a high pressure unit for pressures of 3,000 psi to 6,000 psi, a medium pressure unit for pressures of 1,000 psi to 3,000 psi, and a low pressure unit for pressures of 100 psi to 1,000 psi. The device can be made to handle pressures up to 6,000 psi, which is not uncommon in many commercial scuba air supply sources.

The kit is provided with at least one mechanical adapter that typically comprises a scuba tank connector that allows the yoke from the supply source to be readily connected to the supply and sample device as if it were being connected to a scuba tank for refilling. This saves time and money at the commercial unit in that a typical supply source for a scuba tank uses the exact same adapter for connection to the supply source.

A second mechanical adapter can be provided that is different, being typically used for supplying air to fire fighters' supply tanks.

The unit includes at its inlet side a mechanical connector that allows it to be connected to either a scuba tank adapter or a fire fighter tank adapter, allowing universal use of the sampling kit for either contingency. A simple, mechanical clip that includes O-ring connectors and releases allows either the scuba or fire fighter mechanical adapter to be snapped into place and quickly released.

The air restrictor employed is a rigid disk or cylinder having a very tiny aperture at the central, cylindrical axis fabricated from a plastic or similar type material. The opening size in diameter and length is chosen for an appropriate high, medium, or low pressure supply source to insure that air flow is properly restricted in greatly reducing the pressure in the air flow conduit used in the device. The air restrictor itself can be inserted and mounted permanently in each adapter for either the scuba or fire fighter mechanical connector, so that it is maintained at the supply source for immediate pressure reduction regardless of the adapter selected.

The air flow conduit itself may be of a conventional plastic that is somewhat flexible, yet rigid enough to sustain the air pressures of the system. Typically the air pressure downstream of the air restrictor may be in the realm of 10 to 15 psi above atmospheric pressure.

The filter essentially comprises a disk-shaped particulate trap made of a particular paper-like material. Just before the air filter the air flow conduit line includes an aperture that allows venting should the pressure become excessive in the air flow conduit prior to the filter. This vent allows air to be dumped if it is excessive so that the proper amount of flow through the filter is maintained. The filter itself is known and does not form a part of the invention per se. It collects particulates that are examined at the laboratory for a given fixed volume of air flowing through the filter to which the total particulate content can be evaluated to determine whether the sample is contaminated or not. Once the sample air has passed through the filter, it travels through the air flow conduit into the plastic pouch where it is collected for ultimate transfer. The pouch has an outlet line that includes a one-way pressure relief valve to prevent the pouch from becoming excessively pressurized. The pouch is made of a plastic polyvinyl, flexible material such as a metallic foil that has been coated with plastic and sealed.

To utilize the invention, one would first select a supply source of breathing air, typically from a large tank to be sampled. If the supply source is used to charge scuba tanks, the adapter that fits a scuba tank supply yoke is taken from the kit and snapped into place at the inlet side of the air flow conduit of the device. The supply source yoke is then tightly attached to the adapter so that an air sample is ready to be taken. At this point, the supply tank is turned on, allowing air to flow into the sampling device with a particular predetermined amount of time being selected for leaving the supply tank on. This is predetermined by the overall system dimensions. After the predetermined amount of flow has taken place, the supply is shut off and the yoke from the supply is disconnected from the adapter. The adapter is placed back in the kit and the sample is ready to be mailed in the box of which it is already contained in to the point for analysis.

Typically, the system is mounted in a cardboard box that is approximately 1 ft. long and 6 in. on each side. The sample is collected by its traverse through the air restrictor, the filter, and into the pouch, with the system providing proper pressurization and venting for a predetermined amount of time to insure that the air sample is uniform and that the proper volume for analysis is known. A separate indicia sheet is provided so that the person taking the sample can mark down the air pressure of the source when the sample is taken and other information relevant to the supply.

It is an object of this invention to provide an accurate, non-complex breathing air sampling retrieval kit that can be used for sampling scuba supply sources of breathing air or fire fighting supply sources of breathing air quickly and easily.

And yet another object of this invention is to provide a sample retrieval kit for compressed air that can obtain samples easily and quickly over a large range of supply source pressures between 100 psi and 6,000 psi.

In accordance with these and other objects which will become apparent hereinafter, the instant invention will now be described with particular reference to the accompanying drawings.

DESCRIPTION OF THE PREFERRED EMBODIMENTS

Figure 1:
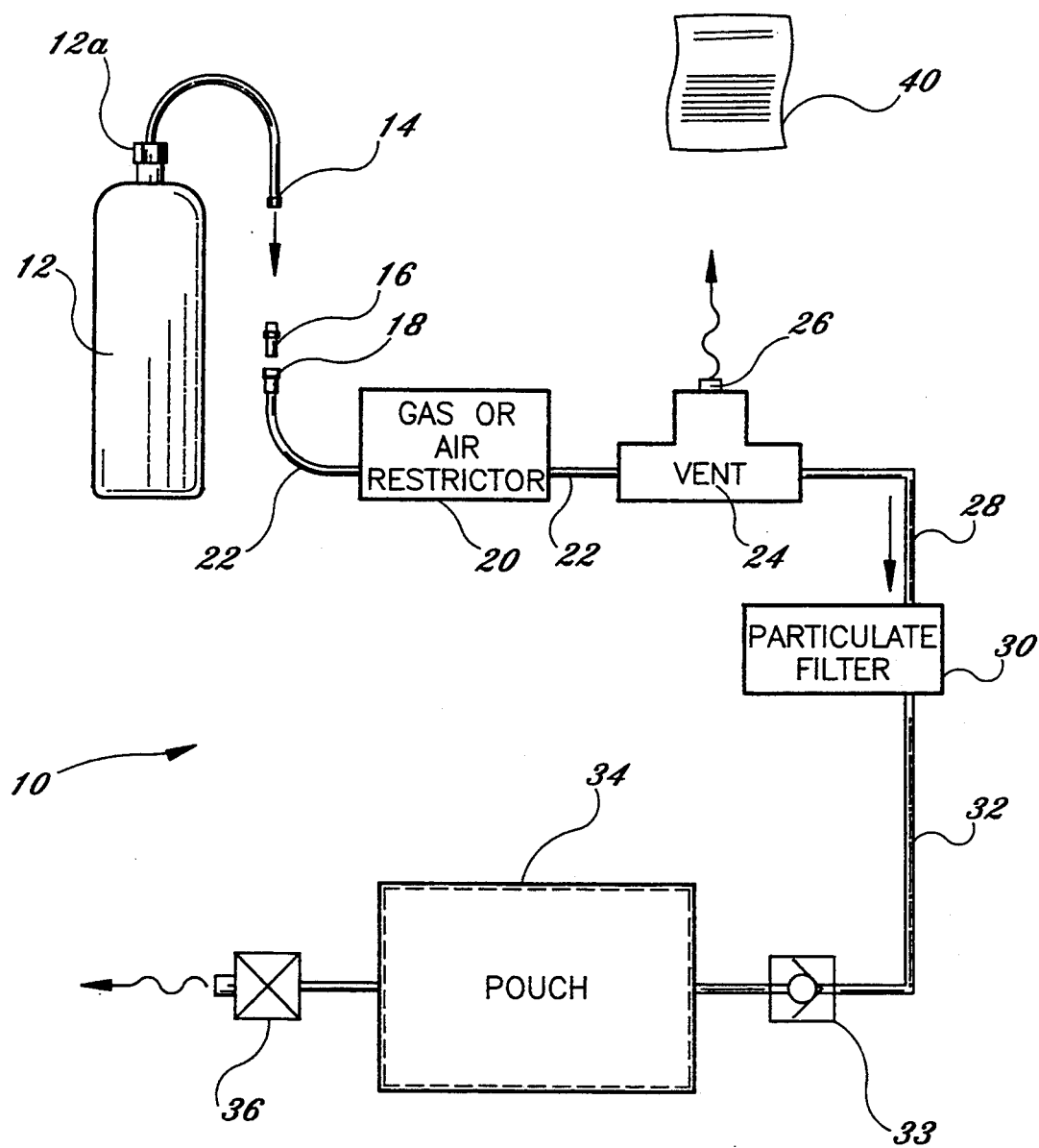
FIG. 1 shows a schematic diagram of the present invention.

Referring now to the drawings and in particular, FIG. 1, the present invention is shown generally at 10, comprising a removable adapter 16 which fits into a manually-actuated connector 18, which is also the inlet to the device for the sample air received from a compressed breathing air supply tank 12. The supply tank 12 has a yoke 14 like that typically found attached to a scuba tank connector for filling a scuba tank, that can fit to a scuba adapter 16 to transfer compressed air located in tank 12 into the inlet supply line over the air flow inlet supply line 22 of the device.

A gas or air restrictor 20 is mounted in the line 22 to greatly reduce the pressure of compressed air in tank 12 so that the system pressure in line 22 is significantly reduced to a working pressure. The exact pressure will be a direct function of the size of the restrictor opening 20, which is described in detail hereto. Connected to the outlet of line 22 is a vent 24 that has an air vent outlet in fluid communication with the outlet of air flow conduit 22 to dump excess air pressure if necessary. This is provided by a direct aperture that exits to ambient air through vent 24. The air flow conduit 28 is connected at its inlet side to vent 24 and its outlet side to a conventional particulate filter 30 that allows air to pass through a filter that collects particulates. The outlet of filter 30 is connected to the inlet of air flow conduit 32 which is in fluid communication with the reservoir or air retrieval pouch 34. The pouch 34 is a sealed foil pouch having a plastic coating that can hold a supply of air under pressure much like an air bladder or the like. The pouch 34 includes a pressure relief valve 36 that allows air under pressure within the pouch to be dumped through the one-way valve 36 when it exceeds a certain pressure.

Figure 2:
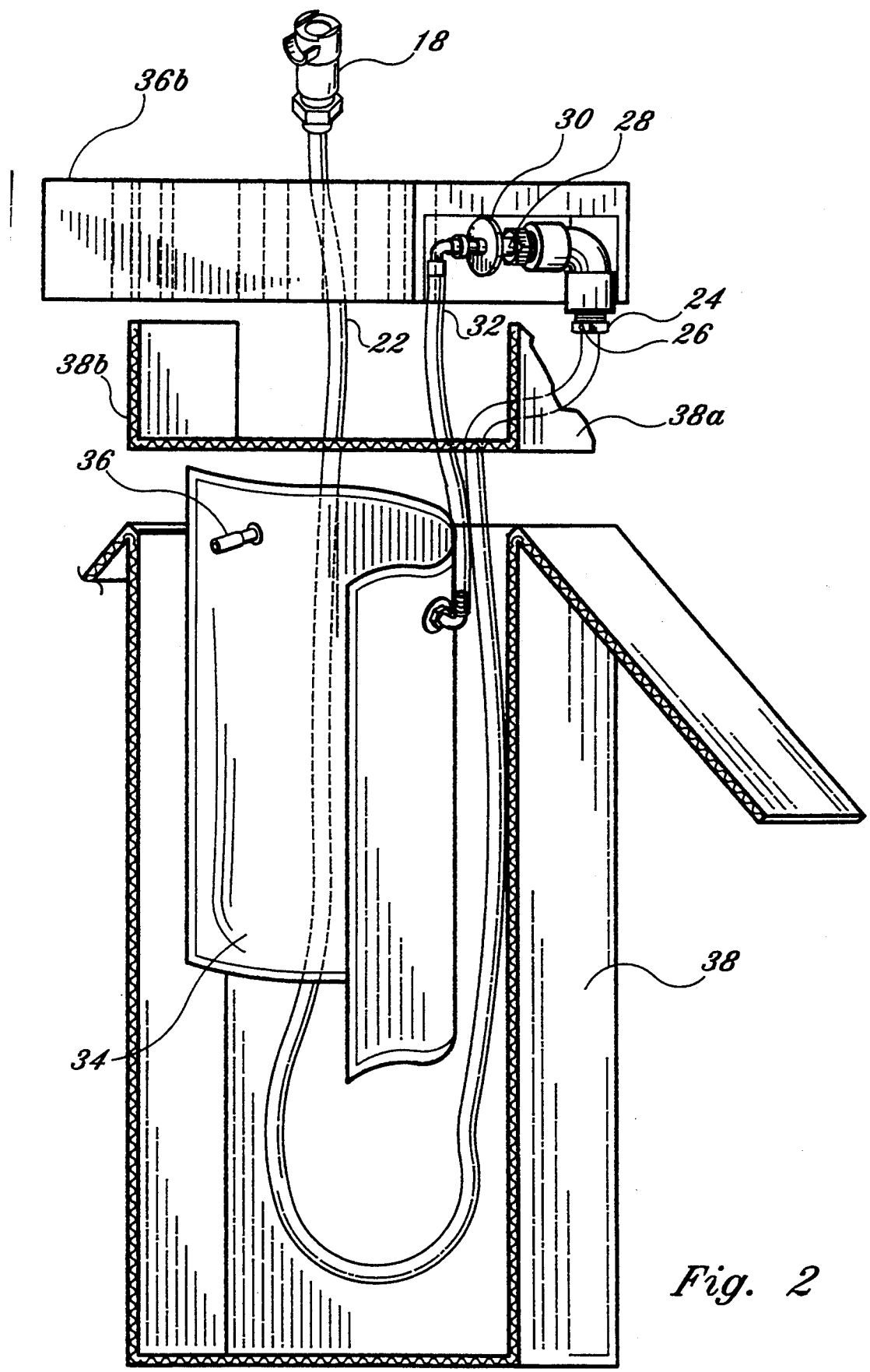
FIG. 2 shows a perspective front view, partially cut away and exploded, of the present invention.

FIG. 2 shows an exploded view of the device which is typically housed in a cardboard box 38 having cardboard pieces 38a and 38b which are mounted down within box 38. Box 38 houses portions of the equipment to provide a kit housing that allows the device to be shipped after the air samples have been taken. The bladder 34 fits comfortably within the cardboard housing 38 even when the bladder has been filled with the air sample. A sponge block 36b also has storage recesses for housing a pair of adapter units which are described below. FIG. 2 shows an air flow conduit 22 that may be pulled out of the box. A connector 18 is provided at the inlet end that is attached to an adapter which hooks to the supply tank that supplies the compressed air to be sampled, retrieved, and ultimately analyzed. The exploded view shown in FIG. 2, in actual operation would have all the parts of the device mounted within housing 38 with the exception that the supply tube 22 would be extended out from the top of the box for retrieving the air sample.

Figure 3:
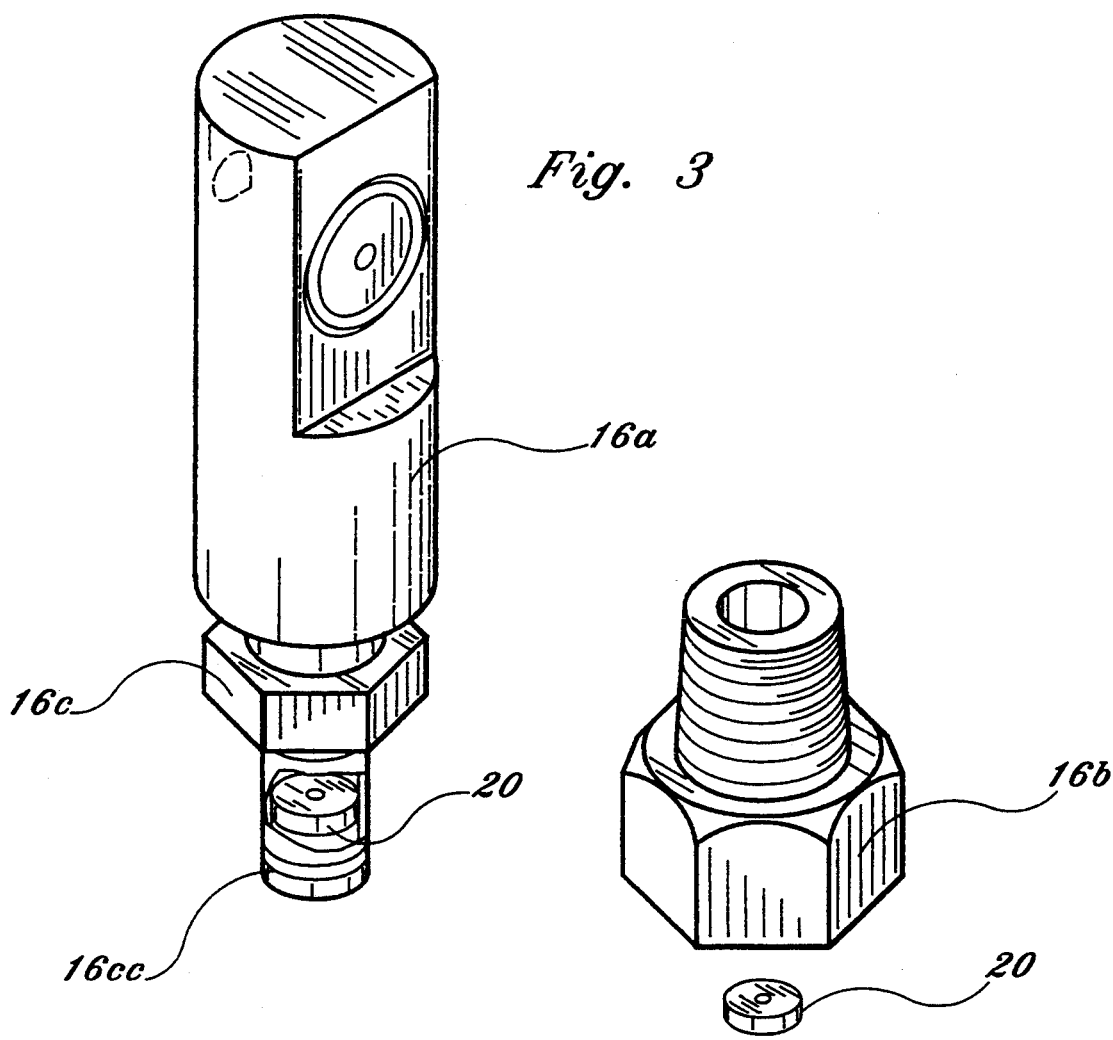
FIG. 3 shows an exploded perspective view of a scuba adapter used with the present invention.
Figure 5:
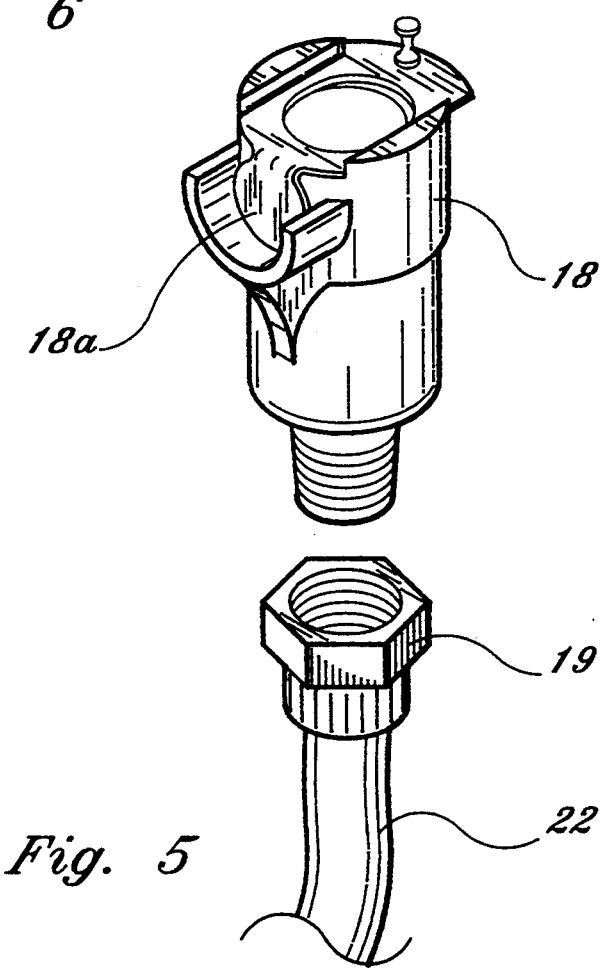
FIG. 5 shows a perspective view, exploded, of a quick-disconnect used with the adapters shown in FIGS. 3 and 4 of the present invention in perspective.

FIG. 3 shows a scuba tank adapter 16a that readily attaches to a supply yoke found attached to a tank of compressed air that would typically be used to fill a scuba tank. Adapter 16a, has a base 16c which includes a push-on, pull-out connecting portion and an air restrictor 20, which is shown as a disk with an aperture in the center. By utilizing adaptor 16a a scuba compressed air supply tank can be quickly attached via the scuba yoke to the adapter 16a without a specialized connection. A connector 18, as shown in FIG. 5, receives the plug-in portion 16c, which is firmly attached to adapter 16a. Connector 18 provides a fluid conduit through base 16c, into manually-actuated fastener disconnect 18 and through a threaded connector 18a so that there is no air loss. The fastener 18 also attaches to the inlet or supply of the air fluid conduit 22

Thus, adapter 16a for scuba tanks includes a threaded connector 16c and an O-ring 16cc, and is manually plugged into connector 18 for taking a sample from a supply tank that has a scuba delivery yoke at its outlet. After the sample has been taken, a manual disconnect 18a is depressed, allowing the connector 16c to be manually pulled from connector 18, disengaging the unit.

Figure 4:
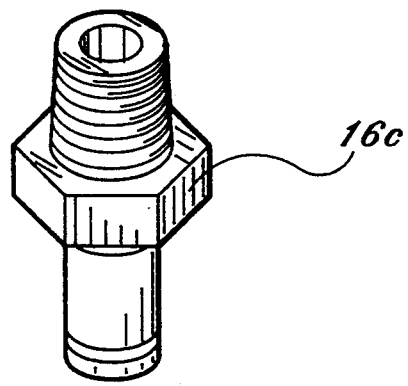
FIG. 4 shows a perspective exploded view of an alternate adapter used with the present invention.

Referring to FIG. 4, a typical connector 16b is shown that comprises an adapter used with fire fighting air tank supply bottles. The connector 16b firmly attaches to the same connector 16c. Thus, 16b adapter and connector 16c are in fluid connection and are threadably attached so that there is no air leak. An air flow restrictor 20 is also mounted in fluid communication with adapter 16b and connector 16c so that as air under pressure is received into adapter 16b it will be greatly diminished in pressure as it passes through air restrictor 20. Connector 16c is manually attached to fastener or mechanical connector 18 in FIG. 5 if one wishes to use the fire fighting supply yoke which attaches to adapter 16b.

Figure 6:
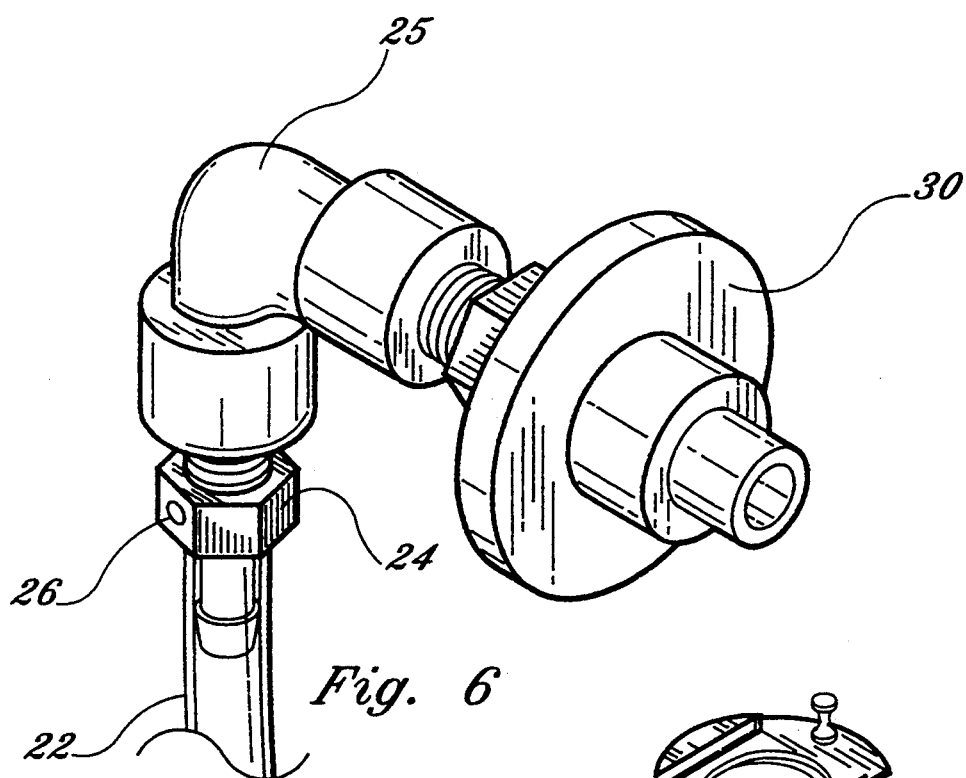
FIG. 6 shows the partial cut away view of a filter and vent used with the present invention in perspective.

FIG. 6 shows a filter 30 attached to an elbow 25. Elbow 24 is connected to a vent 26 that receives the air sample through the inlet air flow conduit 22. Vent 26 provides a hole in fluid communication with the fluid in air flow conduit 22 so that if excess pressure exists, it will be vented out through vent hole 26. This protects and insures the proper flow, especially through filter 30 as the air sample flows through filter 30 and into the pouch 34. The filter 30 is conventional and necessary in the invention to allow analysis of particulate matter found in the air sample. It is necessary that a predetermined amount of air volume flows through filter 30 so that the amount of accumulated contamination can be readily calculated after observation and removal of the filter element from inside filter 30. The filter 30, therefore, is useful in determining particulates in the air supply.

Referring back to FIGS. 1 and 2, in order to retrieve a sample of air under high pressure in tank 12, the proper adapter, either for a scuba yoke or for a fire fighter tank yoke 16, must first be selected. The adapter is housed in the top of the kit in a sponge or sponge-like rack. Thus, an adapter such as 16a or 16b would be selected. Once selected, the adapter is manually positioned into a connector 18 and attached to yoke 14 from the supply line. At this point, the supply tank 12 is opened, allowing high pressure compressed air to flow through yoke 14, through adapter 16, through fastener 18 and through air flow restrictor 20. The pressure in tank 12 is then greatly reduced through air restrictor 20 which is in the air flow conduit 22. The air sample then travels through vent 24 where excess pressure is dumped through vent hole 26 into the ambient air. The air sample continues through air flow conduit 28, through filter 30 and through air flow conduit 32 into retaining pouch 34. Excess air pressure in pouch 34 is dumped through a one-way valve 36 which is normally a pressure relief valve. Typically, the air sample pressure in pouch 34 will be between 5 and 10 psi. In a preferred embodiment, the air restrictor 20 is sized such that an air sample flows from tank 12 under a constant pressure for a prescribed amount of time. Preferably, as an example, this time could be for three minutes exactly. Once the exact time limit has been reached, the air supply 12 is turned off by shutting off air supply valve 12a. A piece of paper bearing indicia that shows the time of flow and the air pressure reading is included with the kit as element 40, which allows one to write down the proper measurements for use during analysis of the air sample.

In view of the fact that the supply tank 12 in commercial usage can have quite a range of breathing air under pressure (anywhere from 100 psi to 6,000 psi), the invention may take the same form but in three different kit sizes. For example, one size could be for 3,000 psi to 6,000 psi; a second size for 1,000 psi to 3,000 psi; and a third size for 100 psi to 1,000 psi. In such cases, the fundamental components are the same, except the air restrictor may be varied in diameter size, while the pressure relief vent may also be changed.

The pouch, 34 should be airtight except for the pressure relief valve and made of a suitable material such as a metal foil that is coated in plastic. The air vent 24 basically is a rigid block having a hole drilled in it that is in fluid communication and connected with the air flow conduits 22 and 28 to act as a vent if the pressure becomes excessive in the line.

The device as shown is non-complex in its structure and operation, allows any user to quickly attach the inlet line to a particular supply source of compressed breathing air, and allows for operation of the device over a great range of different supply pressures, that is, from 100 psi to 6,000 psi. The device is lightweight, fits in a rigid box that can be closed after the sample has been taken and mailed or shipped to the proper place for analysis. The system is completely automatic and does not require complex metering and measuring devices for its accurate operation.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A kit for sampling compressed breathing air from a source of compressed breathing air having pressure ranging from 100 psi to 6,000 psi, said kit comprising:

a housing;

a mounting block mounted in said housing;

air sample receiving pouch for collecting and storing an air sample, said pouch mounted within said housing, said housing capped by said mounting block;

said air sample receiving pouch incorporating a pressure relief valve for relieving excess air pressure;

air flow conduit having an inlet and an outlet, said outlet connected in fluid communication with said air sample receiving pouch;

compressed breathing air source connector means connected to the inlet end of said air flow conduit, for fluidly communicating with said source of compressed breathing air, said compressed breathing air maintained under pressure in a pressure vessel;

air particulate filter connected in fluid communication to said air flow conduit so that air flowing through said conduit passes through said air particulate filter, said filter fluidly connected in series between said conduit inlet and said conduit outlet;

air flow restricting means, in fluid communication and connected to said air flow conduit in series between said conduit inlet and said air filter and in proximity to said connector means, said air flow restricting means for reducing the pressure of said compressed breathing air communicating with said air flow conduit;

air vent means fluidly connected in series to said conduit, between said air flow restricting means and said air filter for venting excess pressure air from said air flow conduit; and an air flow connector adapter for a mating fluid communication connection to a commercial air supply yoke communicating with the source of compressed air for connecting said connector means to said source of compressed breathing air, from which the air sample is to be taken, whereby the air sample is collected from the compressed air source, said housing being transportable to an analysis location and removable for analysis of said sample.

2. A device as in claim 1, wherein a plurality of air flow connector adapters can be individually mounted on said mounting block in said housing.

3. A device as in claim 1, wherein said air flow connector adapter is connectable to a scuba tank air delivery yoke.

4. A device as in claim 1, wherein said air flow connector adapter is connectable to a fire fighting yoke air supply.

* * * * *